United States Patent

Murakami et al.

[11] Patent Number: 5,919,977
[45] Date of Patent: Jul. 6, 1999

[54] PROCESS FOR PRODUCING AROMATIC CARBOXYLIC ACID AND APPARATUS THEREFOR

[75] Inventors: Satoshi Murakami, Iwakuni; Toshiyuki Sakata, Ohtake, both of Japan

[73] Assignee: Mitsui Chemicals, Inc., Tokyo, Japan

[21] Appl. No.: 09/025,628

[22] Filed: Feb. 18, 1998

[30] Foreign Application Priority Data

Feb. 20, 1997 [JP] Japan .................................... 9-036596

[51] Int. Cl.$^6$ .................................................. C07C 51/16
[52] U.S. Cl. ............................................................ 562/412
[58] Field of Search ............................................. 562/412

[56] References Cited

U.S. PATENT DOCUMENTS 4,243,636  1/1981  Shiraki et al. .

FOREIGN PATENT DOCUMENTS

| 0673910 A1 | 9/1995 | European Pat. Off. . |
| 0742043 A2 | 11/1996 | European Pat. Off. . |
| 1129398 | 9/1967 | United Kingdom . |

Primary Examiner—Samuel Barts
Attorney, Agent, or Firm—Birch, Stewart, Kolasch and Birch, LLP

[57] ABSTRACT

A process and an apparatus for producing an aromatic carboxylic acid by a liquid phase oxidation of an alkyl aromatic compound with a molecular oxygen-containing gas in the presence of an oxidation catalyst in a reaction solvent in an oxidation reactor, which process can afford to suppress the amount of non-condensing gas lost in accompaniment with the withdrawn slurry of the formed aromatic carboxylic acid crystals from the oxidation reactor to thereby increase the utilization efficiency of the molecular oxygen-containing gas, wherein a deflector 10 is arranged on the inner surface of the reactor wall at a portion downstream from the opening 9 for the slurry withdrawal line 8 in the flow path of the stirring stream 11 of the reaction liquor and the oxidation is conducted while stirring the reaction liquor by a stirrer 3 and while withdrawing the resulting slurry containing the formed aromatic carboxylic acid crystals from the reactor, by feeding the alkyl aromatic compound together with the reaction solvent and with the catalyst to the reactor via a raw material feed line 6 while supplying the molecular oxygen-containing gas thereto via a gas supply line 7, whereby the amount of the non-condensing gas entrained in the withdrawn slurry from the reactor is suppressed.

3 Claims, 2 Drawing Sheets

5,919,977

PROCESS FOR PRODUCING AROMATIC CARBOXYLIC ACID AND APPARATUS THEREFOR

FIELD OF THE INVENTION

The present invention relates to a process for producing an aromatic carboxylic acid by subjecting an alkyl aromatic compound having one or more substituent alkyl groups or one or more partially oxidized substituent alkyl groups to a liquid phase oxidation by a molecular oxygen-containing gas as well as to an apparatus for realizing such a process.

DESCRIPTION OF THE RELATED TECHNIQUES

Aromatic carboxylic acids are important as basic chemicals and are useful in particular as the starting materials for, such as, textiles, resins and plasticizers. For instance, terephthalic acid have found its increased demand in recent years as raw material for polyesters.

Heretofore, aromatic carboxylic acids have been produced generally by a process comprising subjecting a methyl-substituted aromatic compound to a liquid phase oxidation in a reaction solvent containing a lower aliphatic carboxylic acid, such as acetic acid, with a molecular oxygen-containing gas in the presence of a catalyst composed of a heavy metal compound and a bromine compound. In such a conventional production process, the liquid phase oxidation is realized in a cylindrical oxidation reactor provided on the inner face of its circumferential wall with a buffle and at its central portion with a stirrer by supplying thereto a mixture of the starting alkyl-substituted aromatic compound, such as paraxylene, a reaction solvent, such as acetic acid, and an oxidation catalyst, while feeding thereto a molecular oxygen-containing gas, such as atmospheric air, to produce an aromatic carboxylic acid, such as terephthalic acid.

The aromatic carboxylic acid produced will crystallize in the mother liquor to form a slurry which is withdrawn from the reactor into a slurry receiver vessel, wherefrom it is transferred to purification step. The slurry is withdrawn from the reactor, in general, at its bottom. Since the oxidation is carried out, in general, using atmospheric air, a problem is brought about that a part of non-condensing gas, such as nitrogen and rest of oxygen, is entrained in the withdrawn slurry, resulting in a considerable loss of the molecular oxygen-containing gas.

SUMMARY OF THE INVENTION

An object of the present invention is to provide a process for producing an aromatic carboxylic acid permitting a highly efficient utilization of the molecular oxygen-containing gas by reducing the amount of non-condensing gas lost by being entrained in the slurry of the formed aromatic carboxylic acid crystals withdrawn from the reactor.

Another object of the present invention is to provide an apparatus for producing an aromatic carboxylic acid capable of reducing the amount of non-condensing gas lost by being entrained in the slurry of the formed aromatic carboxylic acid crystals withdrawn from the reactor.

Thus, the process for producing an aromatic carboxylic acid according to the present invention comprises the process steps of introducing an alkyl aromatic compound together with an oxidation catalyst and a reaction solvent via a raw material feed line into an oxidation reactor having the raw material feed line, a molecular oxygen-containing gas supply line, a stirrer, a slurry withdrawal line and a deflector provided in the path of the stream of stirred reaction liquor at a portion downstream from the opening for the slurry withdrawal line disposed on the inner wall of the oxidation reactor to deflect stirred stream of the reaction liquor; supplying thereto a molecular oxygen-containing gas via the molecular oxygen-containing gas supply line to effect a liquid phase oxidation of the alkyl aromatic compound while stirring the reaction liquor by the stirrer to thereby form an aromatic carboxylic acid in a form of a slurry of crystals thereof; and withdrawing the slurry from the reactor through the slurry withdrawal line under suppression of entrainment of non-condensing gas in the withdrawn slurry by the installation of the deflector.

The apparatus for producing an aromatic carboxylic acid according to the present invention comprises an oxidizing reactor for forming an aromatic carboxylic acid by a liquid phase oxidation of an alkyl aromatic camound; a feed line for feeding the alkyl aromatic compound raw material to the reactor together with a reaction solvent and an oxidation catalyst; a gas feed line for feeding a molecular oxygen-containing gas to the reactor; a stirrer for stirring the reaction liquor in the reactor; a slurry withdrawal line for withdrawing the slurry containing the resulting aromatic carboxylic acid from the reactor; and a deflector provided in the path of the stream of stirred reaction liquor at a portion downstream from the opening for the slurry withdrawal line disposed on the inner wall of the oxidation reactor.

DETAILED DESCRIPTION OF THE DISCLOSURE

Figure 1:
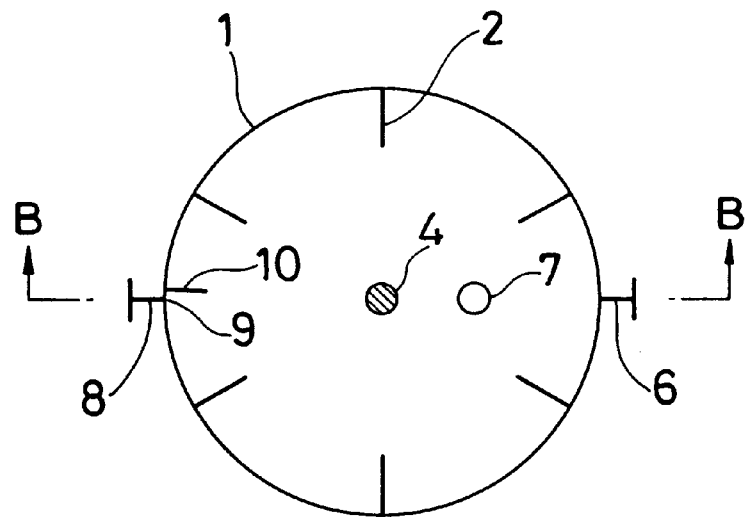
FIG. 1 shows an embodiment of the apparatus for producing aromatic carboxylic acid according to the present invention, wherein FIG. 1($a$) is a sectional plan view along the line A—A of FIG. 1($b$) which is a sectional elevation along the line B—B of FIG. 1($a$).
Figure 1:
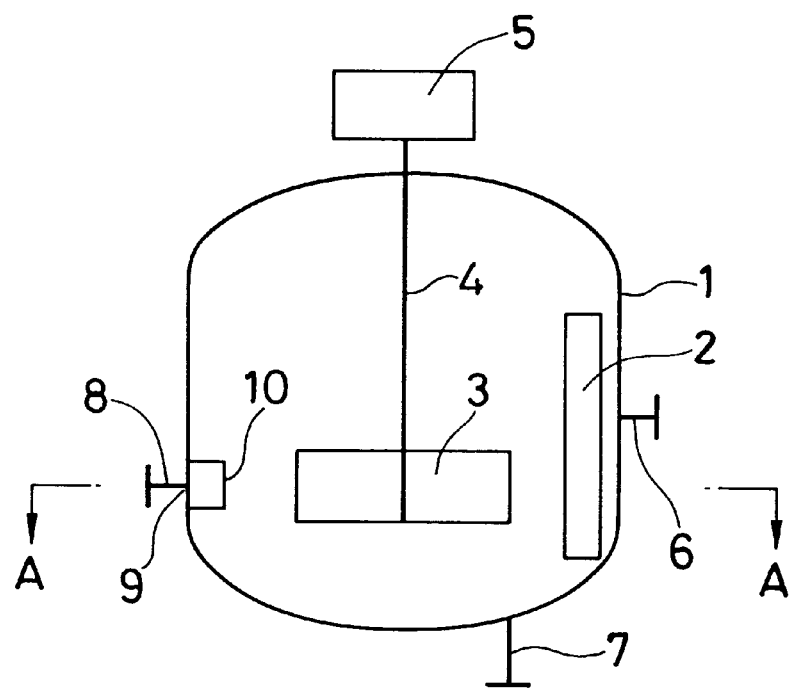

The oxidation reactor to be used according to the present invention is constructed to be adapted to supply an alkyl aromatic compound, a reaction solvent a catalyst and a molecular oxygen-containing gas thereto for realizing a liquid phase oxidation of the alkyl aromatic compound while stirring the reaction mixture to produce an aromatic carboxylic acid. It is preferable that the oxidation reactor has an upright cylindrical configuration, while other form of reactor may also be permissible.

The oxidation reactor is furnished with a raw material feed line to be served for feeding the alkyl aromatic compound, the reaction solvent and the oxidation catalyst to the reactor. The raw material feed line opens into the reactor at a location adapted to communicate to the liquid phase of the reaction mixture, wherein it opens into the reactor preferably at an intermediate portion.

The oxidation reactor is provided with a gas supply line for supplying a molecular oxygen-containing gas thereto. The gas supply line may preferably opens to the oxidation reactor at a lower portion thereof, while it is permissible that it opens to the reactor at other location. The oxygen-containing gas is a molecular oxygen-containing gas, for which oxygen gas or atmospheric air may be exemplified, while air is favorable for pracitical use.

The oxidation reactor has a stirrer for stirring the reaction liquor. While there is no special restriction for the stirrer, a stirrer of a type of rotating stirring vane is preferred. It is preferable to dispose the stirrer so as to locate the stirrer shaft to extend along the central axis of the reactor, in order to produce an agitating flow swirling along the inner surface of the circumferential wall of the reactor. For facilitating the agitating performance, it may be preferable to arrange vertical buffle plates inside the reactor around its circumference.

The oxidation reactor is provided also with a slurry withdrawal line for withdrawing the slurry of the formed aromatic carboxylic acid crystals suspended in the reaction liquor. There is no special limitation for the location of the slurry withdrawal line to open into the reactor, so long as it permits effective withdrawal of the slurry from the reactor, while it is preferable to locate the junction point thereof at a lower portion of the reactor.

According to the present invention, a deflector is provided on the reactor inner wall surface in the flow path of the stirring slurry stream at a portion downstream from the opening for the slurry waithdrawal line. It is enough for the deflector to cause an acceleration of the flow velocity of the slurry stream above the opening for the slurry withdrawal line, in order to suppress entrainment of bubbles of non-condensing gas into the withdrawn slurry and there is no special limitation for the configuration and size thereof, so that even a flat plate will reveal enough function, though other forms, such as curved surface and the like, may also be permissible.

The deflector may have a width of 2–5 times, preferably 2–3 times, the diameter of the opening for the slurry withdrawal line and a height of 1–3 times, prefeably 1–2 times, the diameter of the opening. It is preferable to dispose the deflector at a position distant from the opening for the slurry withdrawal line toward the lower reaches of the stirring stream by a distance of not greater than 3 times, preferably not greater than 0.5 time, the diameter of the opening in such a posture that it stands vertically to the inner wall of the reactor.

As the starting material to be oxidized for the production of the aromatic carboxylic acid according to the present invention (sometimes denoted hereinafter simply as oxidation raw material), aromatic compounds having substituent alkyl group(s) and/or substituent partially oxidized alkyl group(s) may be employed. Such aromatic compounds may be of monocyclic or polycyclic. As the alkyl substituent group, there may be enumerated, for example, alkyl groups having 1–4 carbon atoms, such as, methyl, ethyl, n-propyl, isopropyl and the like. As the partially oxidized alkyl group, for example, formyl, acyl, carboxyl and hydroxyalkyl, may be enumerated.

Concrete examples of the aromatic compound having substituent alkyl groups include di- or polyalkylbenzenes having 2–4 alkyl groups of 1–4 carbon atoms, such as, m-diisopropylbenzene, p-diisopropylbenzene, m-cymene, p-cymene, m-xylene, p-xylene, trimethylbenzene and tetramethylbenzene; di- or polyalkylnaphthalenes having 2–4 alkyl groups of 1–4 carbon atoms, such as, dimethylnaphthalene, diethylnaphthalene, diisopropylnaphthalene and the like; polyalkylbiphenyls having 2–4 alkyl groups of 1–4 carbon atoms, such as dimethylbiphenyl and the like.

The aromatic compounds having one or more partially oxidized alkyl groups are those in which one or more substituent alkyl groups of the above-mentioned alkyl substituent-containing aromatic compounds are partially oxidized into formyl, acyls, carboxyl or hydroxyalkyls. Concrete examples thereof include 3-methylbenzaldehyde, 4-methylbenzaldehyde, m-toluic acid, p-toluic acid, 3-formylbenzoic acid, 4-formylbenzoic acid and formyl-naphthalenes. They may be used solely or in a mixture of two or more of them.

For the catalyst to be used in the process according to the present invention, a heavy metal compound and a bromine compound is employed. Concrete examples of these compounds may be as follows. As the heavy metal for the heavy metal compound, there may be enumerated, for example, cobalt, manganese, nickel, chromium, zirconium, copper, lead, hafnium and cerium. They may be used solely or in a combination, wherein a combination of cobalt with manganese is particularly preferred.

As the compound of such a heavy metal, there may be enumerated, for example, acetate, nitrate, acetylacetonate, naphthenate, stearate and bromide, wherein special preference is given to acetate.

As the bromine compound, there may be enumerated, for example, inorganic bromine compounds, such as, molecular bromine, hydrogen bromide, sodium bromide, potassium bromide, cobalt bromide and manganese bromide; and organic bromine compounds, such as, methyl bromide, methylene bromide, bromoform, benzyl bromide, bromomethyltoluene, dibromoethane, tribromoethane and tetrabromoethane. Also, these bromine compounds may be used solely or in a mixture of two or more of them.

According to the present invention, the catalyst constituted of the combination of the above-mentioned heavy metal compound and the above-mentioned bromine compound may preferably be of those combinations in which one mole of the heavy metal is combined with 0.05–10 moles, preferably 0.1–2 moles of bromine. Such a catalyst may be used usually in an amount in the range from 10 to 10,000 ppm, preferably from 100 to 5,000 ppm as the heavy metal concentration in the reaction solvent.

Concrete examples of the lower aliphatic carboxylic acid to be used as the reaction solvent include acetic acid, propionic acid and butyric acid. The lower aliphatic carboxylic acid may be used either solely or in a mixture with water for the reaction solvent. Concrete examples of the reaction solvent include acetic acid, propionic acid, butyric acid and mixtures of them as well as mixtures of such a lower aliphatic carboxylic acid with water. Among them, preference is given to the mixture of acetic acid with water, wherein a mixture of 1–20 parts, in particular, 5–15 parts by weight of water with 100 parts by weight of acetic acid is especially preferable.

The amount of the reaction solvent to be used may be in the range from 1 to 70 parts by weight, preferably from 2 to 50 parts by weight, especially preferably 2 to 6 parts by weight, per one part by weight of the starting aromatic compound to be oxidized in the liquid phase in the reactor. Thus, the solvent weight ratio may be in the range from 1 to 70, preferably from 2 to 50, especially preferbly 2 to 6. When the amount of the reaction solvent used is in the above-mentioned range, the diffusion of molecular oxygen into the reaction solvent can be promoted, since the solids concentration in the reaction mixture will be low, so that a high reaction rate can be attained with simultaneous attainment of production of a higher quality aromatic carboxylic acid. Due to the attainment of a higher reaction rate, it is also possible to attain a higher feed rate of the starting aromatic compound with a shorter reaction time, whereby the volume efficiency of the reactor becomes higher with an increase in the productivity.

In the process for producing an aromatic carboxylic acid according to the present invention, a mixture of an alkyl aromatic compound, a reaction solvent and a catalyst is fed via the raw material feed line and a molecular oxygen-containing gas is supplied via the gas supply line, respectively, to the oxidation reactor to conduct the oxidation reaction while stirring the reaction mixture by the stirrer. The alkyl aromatic compound as the oxidation raw material is thereby subjected to a liquid phase oxidation by the molecular oxygen-containing gas within the reaction solvent containing a lower aliphatic carboxylic acid in the presence of the catalyst.

Here, the molecular oxygen-containing gas is supplied to the reaction system in excess over the requisite amount for the oxidation of the oxidation raw material, i.e. the aromatic compound into corresponding aromatic carboxylic acid. In case air is emloyed as the molecular oxygen-containing gas, it is preferable to supply air to the reaction system in a proportion of 2–20 N m$^3$ preferably 2.5–15 N m$^3$ per 1 kg of the aromatic compound as the oxidation raw material. The non-condensing gases, such as oxygen, nitrogen and so on, in the molecular oxygen-containing gas circulate together with the stirring stream of reaction liquor within the reactor in a form of bubbles dispersed in the reaction liquor.

By the oxidation, the alkyl aromatic compound is oxidized into corresponding aromatic carboxylic acid, which will precipitate out of the reaction liquid phase as crystals to form a slurry. The slurry is withdrawn from the reactor via the slurry withdrawal line into the slurry receiver vessel, from which it is transferred to the subsequent purification step. Some of the non-condensing gases, such as oxygen and nitrogen dispersed as small bubbles in the reaction liquor may be withdrawn from the reactor by being entrained in the withdrawn stream of the slurry. The withdrawn amount of the non-condensing gas in accompaniment with the withdrawn stream of the slurry can be suppressed by the arrangement of the deflector.

Thus, the slurry containing the product crystals and gas bubbles circulating in the oxidation reactor along the inner surface of the reactor wall due to the stir by the stirrer will be accelerated on flowing around the deflector disposed at a portion downstream from the opening for the slurry withdrawal line in the flow path of the stirring stream. Here, the gas bubbles having low specific weight will tend to be drifted away from the opening on the stirring stream of the slurry, whereby the amount of the non-condensing gas get out together with the withdrawn stream of the slurry is reduced. As a result, the utilization efficiency of the molecular oxygen-containing gas is increased.

On the contrary, when such a deflector is disposed at a portion upstream to the opening in the flow path of the stirring stream of the slurry, the gas bubbles will tend to be sucked in behind the deflector, since this portion is brought to a negative pressure by the detouring flow. As a result, the amount of the non-condensing gas get out of the reactor through the opening for the slurry withdrawal line located in this case downstream from, i.e. behind, the deflector in the slurry flow path will be increased, so that a considerable amount of the molecular oxygen-containing gas supplied to the reactor with expense of cost and energy is lost in vain without being utilized.

According to the present invention, the amount of the non-condensing gas get out of the reactor in accompaniment with the withdrawn slurry via the slurry withdrawal line is reduced by the installation of the deflector at a portion downstream from the opening for the slurry withdrawal line in the flow path of the stirring stream of the slurry, so that the utilization efficiency of the molecular oxygen-containing gas in the reactor becomes increased.

THE BEST MODE FOR EMBODYING THE INVENTION

In the following, the present invention will further be described in more detail by way of embodiments shown in the appended drawings.

FIG. 1 shows an embodiment of the apparatus according to the present invention, in which (a) is a schematic sectional plan view along the line A—A of (b) and (b) is a schematic sectional front view along the line B—B of (a).

Figure 2:
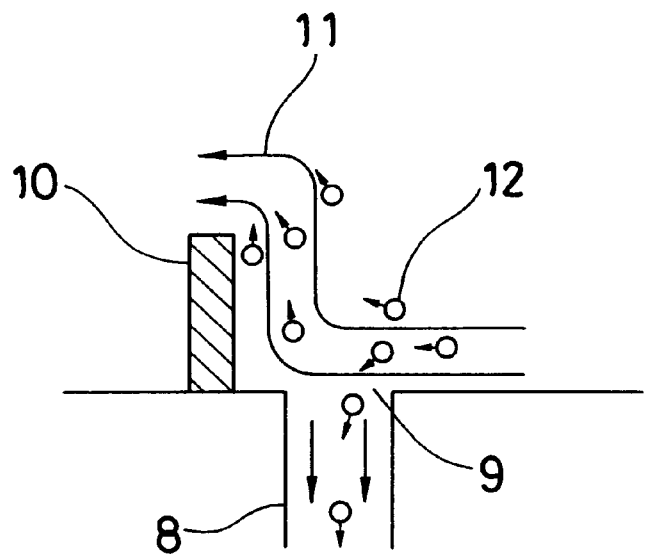
FIG. 2($a$) shows an arrangement of the deflector in a flow path in downstream and FIG. 2($b$) shows an arrangement of the deflector upstream in the flow path.
Figure 2:
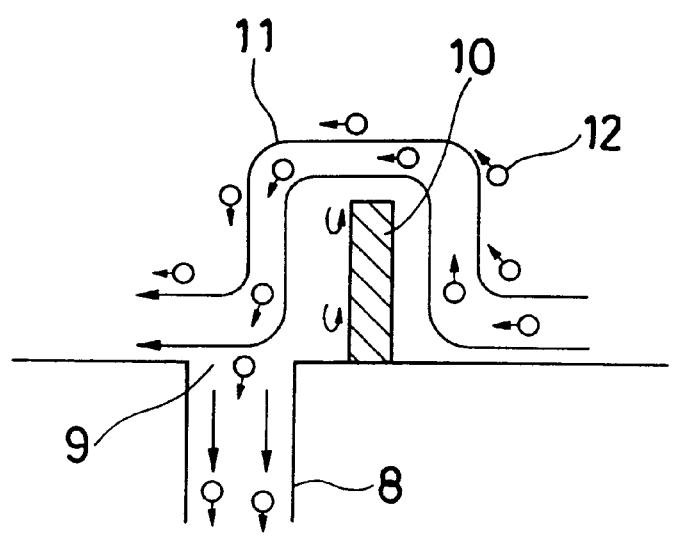

FIG. 2(a) is an explanatory illustration of the apparatus according to the present invention in which the deflector is disposed at a portion downstream from the opening for the slurry withdrawal line in the flow path of stirring stream of slurry. FIG. 2(b) is an explanatory illustration of a comparative apparatus in which the deflector is disposed at a portion upstream to the opening for the slurry wathdrawal line in the flow path of the stirring stream of slurry.

In the apparatus of FIG. 1, the numeral 1 represents the oxidation reactor constructed in a form of an upright cylinder, which is provided, along the inner surface of the circumferential wall, with a buffle 2 extending in vertical direction and, at the central portion thereof, with a stirrer 3 of a rotary vane type having a central rotary shaft 4 driven by a driving unit 5 and extending upwards passing through the upper wall of the oxidation reactor 1.

The oxidation reactor 1 is connected at an intermediate portion on its circumferential wall with a raw material feed line 6 and at its lower portion with a plurality of upwardly directing gas supply lines 7. Remote from the gas supply lines 7, a slurry withdrawal line 8 opens into the oxidation reactor 1. On the inside face of the reactor wall, a flat deflector 10 is arranged at a portion downstream from the opening 9 for the slurry withdrawal line 8 in the flow path of the stirring stream 11 of the reaction liquor, so as to project vertically to the wall surface.

In the process for producing an aromatic carboxylic acid by the apparatus given above, a mixture of an alkyl aromatic compound, a reaction solvent and a catalyst is fed via the raw material feed line 6 and a molecular oxygen-containing gas is supplied via the gas supply line 7, respectively, to the oxidation reactor 1 to conduct the oxidation reaction while stirring the reaction mixture by the stirrer 3 via the driving unit 5. As a result, the alkyl aromatic compound as the oxidation raw material is subjected to a liquid phase oxidation in the reaction solvent comprising a lower aliphatic carboxylic acid by the molecular oxygen-containing gas in the presence of the catalyst.

Here, the molecular oxygen-containing gas is supplied to the reactor in excess of the amount requisite for oxidizing the alkyl aromatic compound into the corresponding aromatic carboxylic acid. The non-condensing gases, such as oxygen, nitrogen and so on, in the molecular oxygen-containing gas circulate inside the reactor together with the stirring stream in a form of bubbles dispersed therein.

The alkyl aromatic compound is oxidized by the reaction to form the corresponding aromatic carboxylic acid which will precipitate as crystals to thereby form a slurry. The slurry is withdrawn from the reactor via the slurry withdrawal line 8 into a slurry receiver vessel, wherefrom it is transferred to the subsequent purification step. Some of the non-condensing gases, such as oxygen, nitrogen and so on, dispersed in the slurry may also be withdrawn in accompaniment therewith. However, the withdrawn amount of the non-condensing gas is reduced by the arrangement of the deflector 10.

Thus, the slurry containing the reaction liquor, the product crystals and the gas bubbles circulating in the oxidation reactor along the inner surface of the reactor wall due to the stirr by the stirrer will be accelerated by the installation of the deflector 10 at a portion downstream from the opening 9 for the slurry withdrawal line 8 in the flow path of the stirring stream 11 upon flowing around it, as illustrated in FIG. 2(a). Here, the gas bubbles 12 will be drifted away from the opening 9 by being carried on the stirring stream 11 of the slurry, whereby the amount of the gas bubbles get out of the reactor via the opening 9 together with the withdrawn slurry is reduced. As a result, the utilization efficiency of the molecular oxygen-containing gas in the reactor 1 is increased.

On the contrary, when the deflector 10 is disposed at a portion upstream to the opening 9 in the flow path of the stirring stream of the slurry, as illustrated in FIG. 2(b), the gas bubbles 12 will tend to be sucked in behind the buffle 10, since this portion is brought to a negative pressure. As a result, a considerable amount of gas bubbles will be get out of the reactor through the opening disposed in this location in accompaniment with the withdrawn slurry, so that the molecular oxygen-containing gas supplied to the reactor 1 with expense of cost and energy is lost in vain without being utilized.

Below, the invention will be decribed by way of Examples.

Reference Example 1

25 liters per hour of paraxylene were fed to the oxidation reactor shown in FIG. 1 (having a capacity of 300 liters, the deflector 10 being lacking) via the raw material feed line, while supplying air thereto at a supply rate of 70 N m$^3$ per hour via the gas supply line 7, in order to effect the oxidation with stirring by the stirrer 3 at a rotational speed of 200 rpm. The formed slurry was withdrawn via the slurry withdrawal line 8 at a withdrawal rate of 200 liters per hour, whereby it was found that the rate of withdrawal of the non-condensing gas due to the entrainment in the slurry relative to that of the total withdrawn slurry amounted to 30% by volume.

Example 1

When the procedures of Reference Example 1 were followed except that a deflector 10 of flat plate of a size of 50 mm length with 70 mm width was arranged on the inner surface of the reactor wall downstream in the flow path of the stirring stream of the slurry at a position 10 cm distant from the opening 9 in the wall of the oxidation reactor 1, whereby it was found that the rate of withdrawal of the non-condensing gas amounted to 15% by volume of that of the total withdrawn slurry.

Referance Example 2

By following the procedures of Example 1 with the exception that the deflector 10 was arranged upstream in the flow path of the stirring stream of slurry, it was found that the rate of withdrawal of the non-condensing gas amounted to 40% by volume of that of the total withdrawn slurry.

What is claimed is:

1. A process for producing an aromatic carboxylic acid, comprising introducing an alkyl aromatic compound together with an oxidation catalyst and a reaction solvent via a raw material feed line into an oxidation reactor, which is provided with the raw material feed line, a molecular oxygen-containing gas supply line, a stirrer, a slurry withdrawal line and a deflector provided in the path of the stream of stirred reaction liquor at a portion downstream from the opening for the slurry withdrawal line disposed on the inner wall of the oxidation reactor to deflect stirred stream of the reaction liquor, supplying thereto a molecular oxygen-containing gas via the molecular oxygen-containing gas supply line to effect a liquid phase oxidation of the alkyl aromatic compound while stirring the reaction liquor by the stirrer to thereby form an aromatic carboxylic acid in a form of a slurry of crystals thereof and withdrawing the slurry from the reactor through the slurry withdrawal line under suppression of entrainment of non-condensing gas in the withdrawn slurry by the installation of the deflector.

2. A process as claimed in claim 1, wherein the alkyl aromatic compound is paraxylene and the aromatic carboxylic acid is terephthalic acid.

3. A process as claimed in claim 1 or 2, wherein the deflector is adapted to accelerate the flow of the slurry around it to thereby causing the gas bubbles to be drifted away from the opening for the slurry withdrawal line by being carried on the stirring stream of the reaction liquor, whereby the amount of gas bubbles entrained in the withdrawn slurry is decreased.

* * * * *